US010635779B2

(12) United States Patent
Ukis (10) Patent No.: US 10,635,779 B2
(45) Date of Patent: Apr. 28, 2020

(54) DEVICES, METHODS AND COMPUTER READABLE MEDIUMS FOR FLEXIBLE DELIVERY AND DEPLOYMENT OF MEDICAL APPLICATIONS (71) Applicant: Siemens Healthcare GmbH, Erlangen (DE)

(72) Inventor: Vladyslav Ukis, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 809 days.

(21) Appl. No.: 15/216,795

(22) Filed: Jul. 22, 2016

(65) Prior Publication Data
US 2017/0132378 A1  May 11, 2017

Related U.S. Application Data (60) Provisional application No. 62/198,329, filed on Jul. 29, 2015.

(51) Int. Cl.
*G06F 9/44* (2018.01)
*G06F 9/445* (2018.01)
(Continued)

(52) U.S. Cl.
CPC .......... *G06F 19/324* (2013.01); *G06F 16/214* (2019.01); *G06F 16/252* (2019.01);
(Continued)

(58) Field of Classification Search
CPC .... G06F 9/44505; G06F 9/445; G06F 9/4856; G06F 9/501; G06F 9/455; G06F 8/61;
(Continued)

(56) References Cited

U.S. PATENT DOCUMENTS 7,779,034 B2 * 8/2010 Pedersen ................. G06F 16/10
707/781
8,843,935 B2 * 9/2014 Hegdal ............... G06F 11/0712
718/104
(Continued)

OTHER PUBLICATIONS

Americo Sampaio et al., Uni4Cloud: an approach based on open standards for deployment and management of multi-cloud applications, May 22, 2011, [Retrieved on Dec. 11, 2019]. Retrieved from the internet: <URL: https://dl.acm.org/citation.cfm?id=1985504> 7 Pages (15-21) (Year: 2011).*

(Continued)

*Primary Examiner* — Anibal Rivera
(74) *Attorney, Agent, or Firm* — Harness, Dickey & Pierce, P.L.C.

(57) ABSTRACT

According to one example embodiment, a remote server includes a memory configured to store computer-readable instructions, and a processor. The processor is configured to execute the computer-readable instructions for installing a medical application at a target destination by determining a deployment configuration of the target destination, determining whether to transform the medical application prior to installing the medical application at the target destination based on the determined deployment configuration of the target destination, and deploying at least one of the medical application or a transformed version of the medical application to the target destination.

16 Claims, 3 Drawing Sheets (51) Int. Cl.
*G06F 11/07* (2006.01)
*G06F 17/30* (2006.01)
*G06F 19/00* (2018.01)
*G06F 16/25* (2019.01)
*G06F 16/28* (2019.01)
*G06F 16/21* (2019.01)
*G06F 9/455* (2018.01)
*H04L 29/08* (2006.01)

(52) U.S. Cl.
CPC ............ *G06F 16/289* (2019.01); *G06F 9/455* (2013.01); *G06F 11/0712* (2013.01); *H04L 67/104* (2013.01)

(58) Field of Classification Search
CPC ... G06F 8/64; G06F 8/60; G06F 11/30; G06F 11/0712; G06F 8/70; G06F 8/65; G06F 8/71; G06F 8/34; G06F 8/20; G06F 8/62; G06F 11/36; G06F 11/079; G06F 11/3676; G06F 11/3696; G06F 11/263; G06F 9/45504; G06F 8/10; G06F 11/3692; G06Q 10/06; H04L 41/22
See application file for complete search history.

(56) References Cited

U.S. PATENT DOCUMENTS

| | | | | |
|---|---|---|---|---|
| 8,997,088 B2* | 3/2015 | Gurikar | | G06F 8/61 717/168 |
| 9,733,921 B1* | 8/2017 | Saenz | | G06F 8/60 |
| 10,248,523 B1* | 4/2019 | Dalal | | G06F 3/0631 |
| 2003/0028589 A1* | 2/2003 | Hittleman | | G06F 8/10 709/203 |
| 2005/0149537 A1* | 7/2005 | Balin | | G06F 16/214 |
| 2006/0074618 A1* | 4/2006 | Miller | | G06F 9/45504 703/13 |
| 2006/0112109 A1* | 5/2006 | Chowdhary | | G06F 16/289 |
| 2006/0168436 A1* | 7/2006 | Campbell | | G06Q 10/06 713/1 |
| 2009/0282067 A1* | 11/2009 | Bendigeri | | G05B 19/042 |
| 2011/0010700 A1* | 1/2011 | Lanner | | G06F 9/44505 717/170 |
| 2011/0225575 A1* | 9/2011 | Ningombam | | G06F 8/65 717/170 |
| 2012/0185913 A1* | 7/2012 | Martinez | | G06F 9/455 726/1 |
| 2013/0007216 A1* | 1/2013 | Fries | | G06F 9/4856 709/218 |
| 2013/0047150 A1* | 2/2013 | Malasky | | G06F 8/61 717/176 |
| 2013/0297964 A1* | 11/2013 | Hegdal | | G06F 11/0712 714/2 |
| 2014/0130036 A1* | 5/2014 | Gurikar | | G06F 8/61 717/176 |
| 2014/0278623 A1* | 9/2014 | Martinez | | G06Q 10/06 705/7.12 |
| 2014/0280961 A1* | 9/2014 | Martinez | | H04L 41/5054 709/226 |
| 2015/0046389 A1* | 2/2015 | Dhayapule | | G06F 11/079 707/602 |
| 2015/0199197 A1* | 7/2015 | Maes | | G06F 8/71 717/122 |
| 2016/0134476 A1* | 5/2016 | Kerber | | H04L 67/104 709/221 |
| 2016/0139902 A1* | 5/2016 | Dimitrakos | | G06F 8/61 717/120 |
| 2016/0139915 A1* | 5/2016 | Dimitrakos | | G06F 8/61 717/126 |
| 2016/0139938 A1* | 5/2016 | Dimitrakos | | G06F 9/44505 718/100 |
| 2016/0140209 A1* | 5/2016 | Dimitrakos | | G06F 11/3692 707/740 |
| 2016/0147518 A1* | 5/2016 | Dimitrakos | | G06F 8/61 717/120 |
| 2016/0147522 A1* | 5/2016 | Dimitrakos | | G06F 8/61 717/174 |
| 2016/0294969 A1* | 10/2016 | Ghosh | | H04L 69/08 |
| 2016/0299835 A1* | 10/2016 | Jain | | G06F 11/3676 |
| 2016/0330082 A1* | 11/2016 | Bliss | | H04L 41/22 |
| 2018/0081644 A1* | 3/2018 | Sahoo | | G06F 8/20 |
| 2018/0285353 A1* | 10/2018 | Ramohalli Gopala Rao | | G06F 9/45558 |
| 2019/0138280 A1* | 5/2019 | Ma | | G06F 8/34 |
| 2019/0273778 A1* | 9/2019 | Mordani | | H04L 67/1044 |

OTHER PUBLICATIONS

Patrick G. Edgett et al., Representation and validation of domain and range restrictions in a relational database-driven ontology maintenance system, Aug. 16-18, 2010, [Retrieved on Dec. 11, 2019]. Retrieved from the internet: <URL https://dl.acm.org/citation.cfm?> 7 Pages (98-104) (Year: 2010).*

* cited by examiner

DEVICES, METHODS AND COMPUTER READABLE MEDIUMS FOR FLEXIBLE DELIVERY AND DEPLOYMENT OF MEDICAL APPLICATIONS

CROSS-REFERENCE TO RELATED APPLICATIONS

This application claims priority under 35 U.S.C. § 119(e) to U.S. provisional patent application No. 62/198,329 filed on Jul. 29, 2015, the entire content of which is hereby incorporated by reference.

BACKGROUND

Deployment of medical applications (provided in form of software) in medical systems used at medical facilities such as hospitals, medical laboratories, etc., may be subject to certain requirements and restrictions. One such requirement and/or restriction may be patient data protection regulations of the country/state in which the medical facility that is using the underlying medical application(s) is located.

Deployment of a medical application may be done in a global data center, a country-specific data center and/or locally in at given medical facilities IT structure/data center.

Conventionally, the most flexible deployment mechanism for deployment of medical applications is deployment at a global data center in which one scalable application installation can support customers (e.g., medical facilities using the medical application installed on the global data center) from around the globe. However such a flexible deployment mechanism may be incompatible with restrictions that are required to be observed by medical facilities in different countries.

The next most flexible deployment mechanism for deployment of medical applications is deployment at a country-specific data center, where such a data center and its operation are in line with regulations and restrictions imposed by the underlying country on medical facilities operating therein. In this case, a medical application vendor may have to maintain one data center in each country in which the vendor's medical application is utilized.

The least flexible conventional deployment mechanism for deployment of medical applications is deployment at a data center local to and exclusively utilized by a given medical facility. This least flexible deployment mechanism is the most common mechanism used today for deploying medical applications, while at the same time it is the most expensive deployment mechanism as it requires the medical applications' vendors to support each and every customer (e.g., medical facility) independently.

However, due to a dynamic change in local, country-wide and/or global rules and restrictions required to be observed by medical facilities around the world, the use of any of the above described deployment mechanisms proves inefficient, cost prohibitive and/or impractical.

SUMMARY

At least one example embodiment relates to methods, devices, and/or computer program products for flexible transformation and deployment of medical applications at target destinations.

According to one example embodiment, a remote server includes a memory configured to store computer-readable instructions, and a processor. The processor is configured to execute the computer-readable instructions for installing a medical application at a target destination by determining a deployment configuration of the target destination, determining whether to transform the medical application prior to installing the medical application at the target destination based on the determined deployment configuration of the target destination, and deploying at least one of the medical application or a transformed version of the medical application to the target destination.

According to yet another example embodiment, the deployment configuration of the target destination is at least one of a platform as a software (PaaS) deployment, infrastructure as a software (IaaS) deployment and a local server deployment.

According to yet another example embodiment, the processor is further configured to execute the computer-readable instructions to transform the medical application into the transformed version of the medical application, if the deployment configuration of the target destination is different from a deployment configuration of the medical application stored in the memory.

According to yet another example embodiment, the processor is further configured to execute the computer-readable instructions to transform the medical application by transforming storage access in the medical software in accordance with the deployment configuration of the target destination, and transforming database access in the medical software in accordance with the deployment configuration of the target destination.

According to yet another example embodiment, the processor is configured to execute the computer-readable instructions to transform the storage access in the medical application by, determining a type of storage at the target destination, and setting the storage access in the medical application to enable access to the type of the storage at the target destination.

According to yet another example embodiment, the processor is configured to set the storage access in the medical application via a storage abstraction layer of the medical application.

According to yet another example embodiment, the type of the storage in the target destination is at least one of a platform as a service (PaaS) blob storage, network attached storage and a local file system.

According to yet another example embodiment, the processor is configured to execute the computer-readable instructions to transform the database access in the medical application by, determining a type of database at the target destination, and setting the database access in the medical application to enable access to the type of the database at the target destination.

According to yet another example embodiment, the processor is configured to set the database access in the medical application via a database abstraction layer of the medical application.

According to yet another example embodiment, the type of the database in the target destination is at least one of a platform as a service (PaaS) managed database, centrally installed database server and a locally installed database.

According to yet another example embodiment, the processor is further configured to execute the computer-readable instructions to store a copy of the medical application or a copy of the transformed version of the medical application on the memory.

According to yet another example embodiment, the processor is further configured to execute the computer-readable instructions to verify successful deployment of the medical application or the transformed version of the medical application.

According to yet another example embodiment, if the processor fails to verify the successful deployment of the medical application or the transformed version of the medical application, the processor is configured to execute the computer-readable instructions to redeploy the copy of the medical application or the copy of the transformed version of the medical application to the target destination.

According to yet another example embodiment, the processor is further configured to execute the computer-readable instructions to complete routine updates of the medical application prior to transforming the medical application if the processor determines that the medical application is to be transformed prior to deployment to the target destination.

According to yet another example embodiment, the processor is further configured to execute the computer-readable instructions to receive the deployment configuration of the target destination from an operator of the target destination for determining whether to transform the medical application or not.

According to yet another example embodiment, the target destination is a medical facility.

According to yet another example embodiment, the medical application is software used for maintaining, analyzing and tracking patient data.

According to yet another example embodiment, the hospital utilizes at least one of a local server, a globally accessible server or a country-wide accessible server for obtaining and utilizing the medical application.

BRIEF DESCRIPTION OF THE DRAWINGS

In the detailed description of example embodiments given herein below and the accompanying drawings, like elements are represented by like reference numerals, which are given by way of illustration only and thus are not limiting of example embodiments and wherein.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF EXAMPLE EMBODIMENTS

While example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the claims. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium. A processor(s) will perform the necessary tasks.

Specific structural and functional details disclosed herein are merely representative for purposes of describing example embodiments of the present invention. Example embodiments may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art.

In the following description, illustrative embodiments will be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include processing circuitry such as one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

In some environments, individual software application elements are processed by a user in a defined sequence. The individual software-application building blocks (e.g., tasks) and sequence of tasks are configured. A sequence of tasks is referred to as a task flow or a workflow. Task flows (or workflows) define both a position of the tasks and the data links between the tasks. The data links ensure that the output data of one task function is used as input data for a subsequent task. Tasks can typically be executed sequentially, in parallel, or in an arbitrary sequence.

Example embodiments provide methods, apparatuses and/or computer readable storage mediums for flexible transformation and deployment of medical applications at target destinations (which may also be referred to as clients such as medical facilities) such that when the medical applications are deployed and utilized at such target destinations, restrictions and regulatory guidelines applicable to (governing) the target destinations are complied with by for example, responsible authorities entities in charge of operating/running the target destinations.

Figure 1:
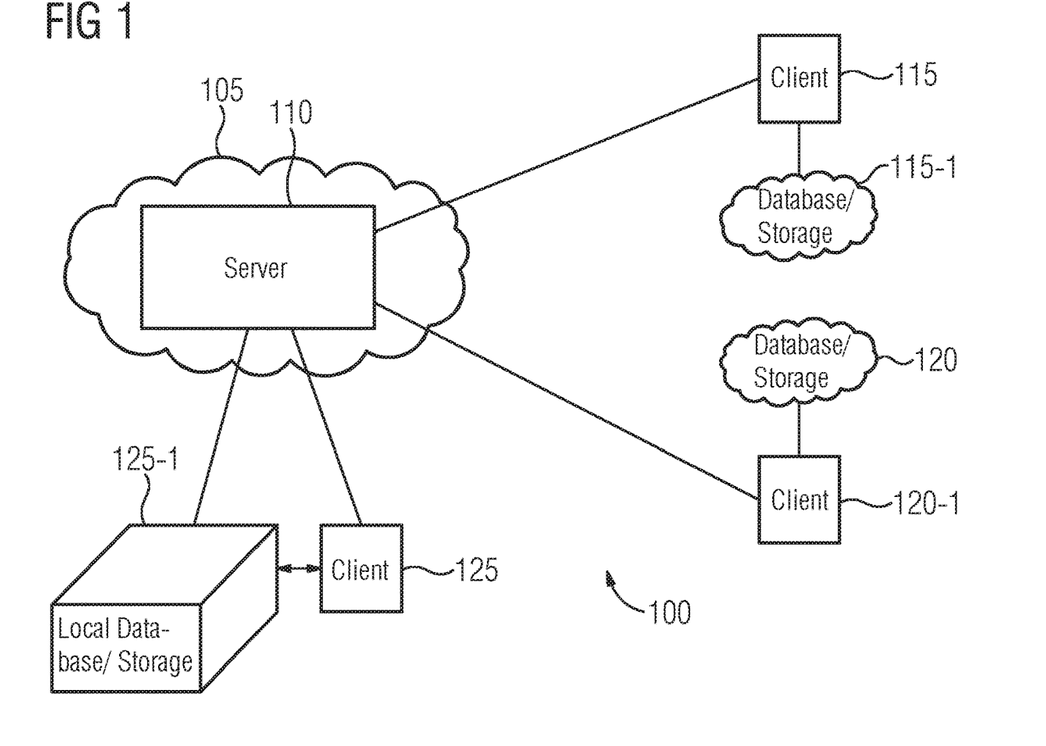
FIG. 1 illustrates a system according to an example embodiment.

FIG. 1 illustrates a system according to an example embodiment. The system 100 shown in FIG. 1 includes a cloud infrastructure 105 having an associated server 110. While FIG. 1 illustrates the cloud infrastructure 105 as including only the server 110, the cloud infrastructure 105 may include any number of additional components/elements that, as commonly known in the art, are used for proper operation and utilization of the cloud infrastructure 105.

The cloud server 110 may be accessible via any known or to be developed methods, by any number of remote clients (target destinations) such as medical facilities 115, 120 and 125. The cloud server 110 may further communicate with database and storage facilities corresponding to each of the clients 115, 120 and 125, either independently or through the corresponding one of the clients 115, 120 and 125, as shown in FIG. 1.

Each of the medical facilities 115, 120 and 125 may have an associated database and storage facility. For example, the medical facility 115 may have the database and storage facility 115-1 associated therewith. The database and storage facility 115-1 may be accessible via a cloud service and may support various types of deployment configurations such as platform as a service (PaaS) deployment, infrastructure as a service (IaaS) deployment, software as a service (SaaS) deployment, etc. Furthermore, the database and storage facility 115-1 may be accessible globally, in a given region, in a given country, in a given state/city, etc.

Similarly, the medical facility 120 may have the database and storage facility 120-1 associated therewith. The database and storage facility 120-1 may be accessible via a cloud service and may support various types of deployment configurations such as platform as a service (PaaS) deployment, infrastructure as a service (IaaS) deployment, software as a service (SaaS) deployment, etc. Furthermore, the database and storage facility 120-1 may be accessible globally, in a given region, in a given country, in a given state/city, etc.

In contrast to the medical facilities 115 and 120, the medical facility 125 may have a local database and storage facility 125-1 associated therewith. A local database and storage facility may refer to a database and storage facility that is accessible by a given/specific medical facility, but inaccessible to any other medical facility.

A medical facility may include, but is not limited to, a hospital, a medical laboratory, etc. Furthermore, while three medical facilities 115, 120 and 125 are shown in FIG. 1, the number of medical facilities that may access cloud infrastructure 105 is not limited thereto. Rather, any number of medical facilities may access medical applications provided on the server 110.

The cloud infrastructure 105 may be provided by a vendor or be utilized by a vendor. The vendor may hereinafter be referred to as a developer, manufacturer and/or distributor of medical applications/software to be deployed at and used by various clients such as clients 115, 120 and 125. The medical application may be one or more software products used for maintaining, analyzing and tracking patient data.

Figure 2:
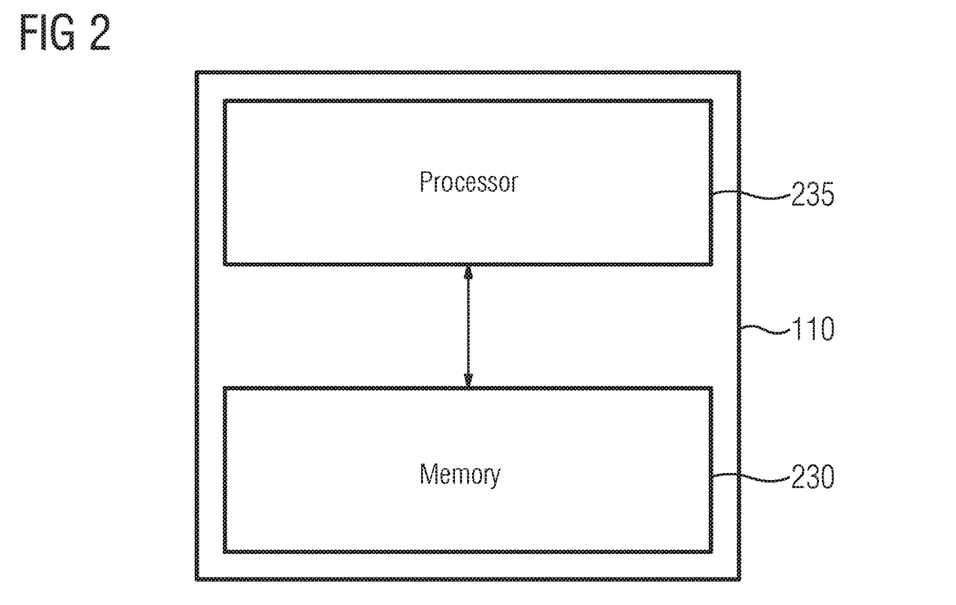
FIG. 2 illustrates the structure of the server associated with the cloud infrastructure shown in FIG. 1, according to an example embodiment.

FIG. 2 illustrates the structure of the server associated with the cloud infrastructure shown in FIG. 1, according to an example embodiment. The server 110 shown in FIG. 2 is the same as the server 110 shown in FIG. 1 and described above. The server 110 may include, among other known or to be developed components, a memory 230 and a processor 235.

The memory 230 may have stored thereon one or more sets of instructions. The one or more sets of instructions may be provided for management and servicing of client(s) accessing the cloud infrastructure 105. Furthermore, the one or more sets of instructions may be provided for the processor 235 to control deployment of and/or manage software-based products for client(s) utilizing such software-based products. Moreover, the software-based products such as medical applications to be provided to client(s) may initially be stored on the memory 230 for deployment to requesting client(s).

The processor 235 may be configured to execute the one or more sets of instructions stored in the memory 230. Furthermore, the processor 235 may be configured to execute updating, transformation and/or deployment of software-based products such as the medical applications described above. Accordingly, the execution of the one or more instructions by the processor 235, transforms the server 110 into a special purpose server for updating, managing, transforming and/or deploying software-based products such as medical application at various client sites such as medical facilities described above.

In one example embodiment, the server 110 may have a plurality of virtual machines/software (environment) stored thereon, each of which may correspond to one of the clients. Each of the virtual machines, under the control of the processor 235, may perform a transformation of medical applications, if applicable, prior to deployment of the medical applications to the corresponding client.

Furthermore, the server 110 may communicate with clients 115, 120 and/or 125 (and/or alternatively, corresponding ones of database and storage facilities 115-1, 120-1 and 125-1) via any known, or to be developed, wired and wireless communications methods.

As described above, a vendor may have a flexible version of a particular software product such as a medical application available on the server 110 to be purchased, subscribed to, etc., by one or more clients such as clients 115, 120 and 125. The medical application available on the server 110 may initially be configured to be compatible for a particular type of deployment configuration at a database and storage facility associated with a client. For example, the medical application available on the server 110 may initially be configured to be compatible with one of various types of deployments including, but not limited to, a PaaS deployment, IaaS deployment, SaaS deployment, etc.

As will be described below, the processor 235 of the server 110 determines whether the software available on the server 110 is to be transformed to be compatible with the deployment configuration/procedure supported by the database and storage facility associated with a particular client. Depending on the determination, the processor 235 may proceed with deploying the medical application or a transformed version of the medical application at the database and storage facility associated with the particular client.

The above-described procedure allows for a more cost-efficient/flexible deployment of medical applications at various medical facilities depending on the deployment configuration supported by the medical facilities, where the supported deployment configuration allows for the medical facilities to comply with individual, local, national and/or global regulations and constraints such as patient data protection rules and regulations.

For example, a specific national regulation may require patient data to be stored only within a medical facility at which a patient is examined/treated. Accordingly, the appropriate deployment configuration ensures that the storing of patient data is only implemented at a corresponding medical facility thus enabling the medical facility to comply with the corresponding country's national regulations.

As will be described in more detail below, the processor 235 may perform further tasks such as software update prior to deployment, storing transformed versions of medical applications, testing successful deployment of the medical applications at the client's database and storage facility, etc.

Figure 3:
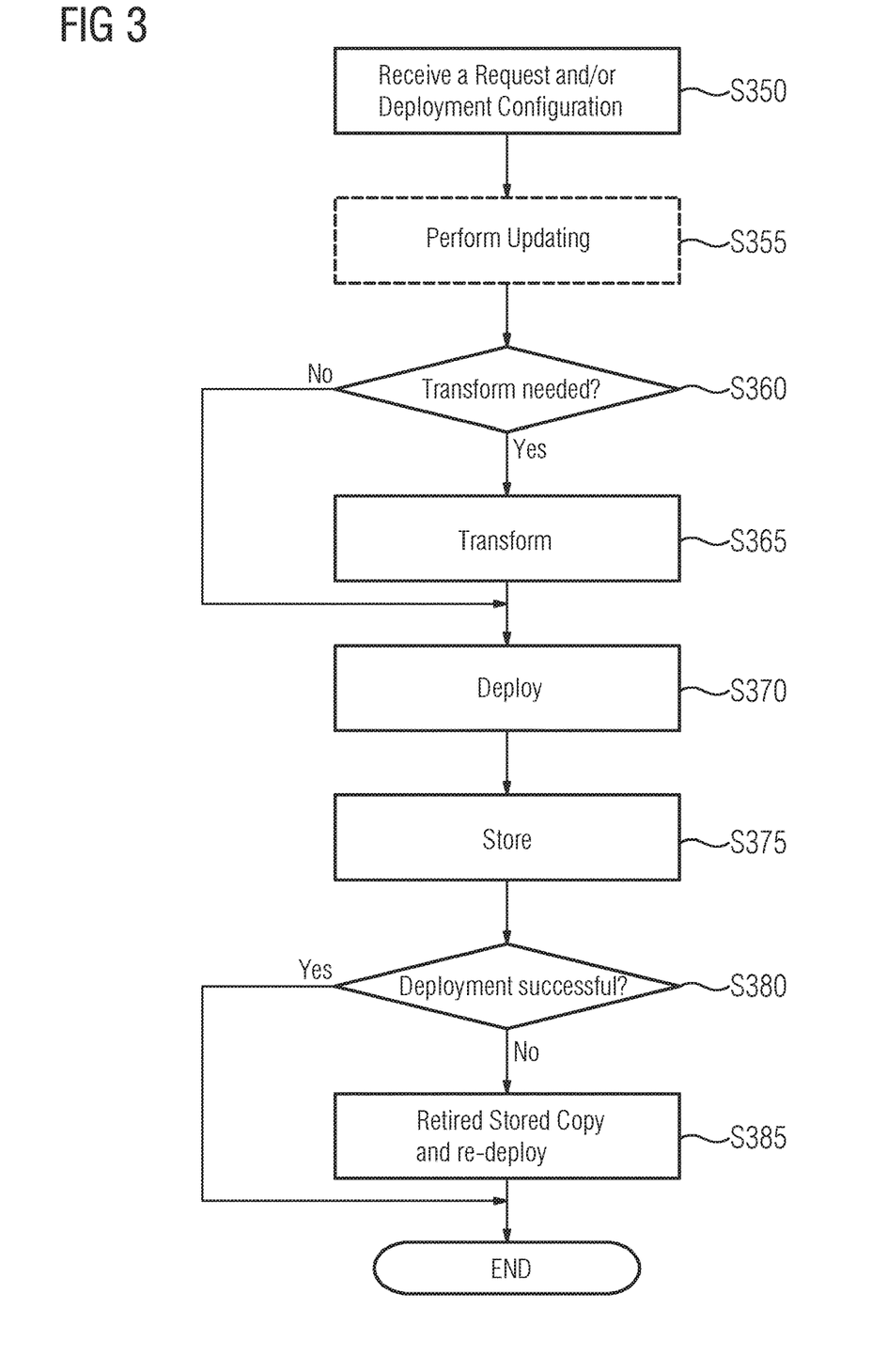
FIG. 3 is a flowchart of a process performed by the server of FIG. 1 for deploying software applications at one or more clients, according to an example embodiment.

FIG. 3 is a flowchart of a process performed by the server of FIG. 1 for deploying software applications at one or more clients, according to an example embodiment.

At S350, the processor 235 of the server 110 may receive a request from a client such as medical facility (target destination) for a particular medical application. The client may be any one of the clients 115, 120 and/or 125 described above with reference to FIG. 1. The request may be a first-time request for purchasing and/or subscribing to the medical application. The request may alternatively be a continuing request for an updated version of the medical application.

In at least one example embodiment, in addition to receiving the request for the medical application, the processor 235 may receive a particular deployment configuration supported by the requesting client. The request including the deployment configuration of the requesting client may be sent to the server 110 by any of the clients 115, 120 and/or 125, using known messaging/communication protocols and standards.

At an optional step S355, the processor 235 may perform any necessary and applicable updating of the medical application(s) as currently available on the server 110 for deployment to a requesting client. While in FIG. 3, the updating is illustrated as being performed after S350, the updating of the medical applications by the processor 235 is not limited to being performed after receiving the request from the client at S350, but may rather be performed at any other point (e.g., before receiving the request from the client, after completion of deployment of the medical application at the client, etc.).

At S360, the processor 235 determines whether to transform the medical application stored on the memory 230 and currently available for deployment to the database and storage facility associated with the requesting client.

In at least one example embodiment, the processor 235 determines whether to transform the medical application by comparing the deployment configuration of the medical application currently available on the server 110 for deployment with the deployment configuration of the requesting client, which may be known to the processor 235 via the request received by the processor at S350, as described above.

For example, the deployment configuration of the medical application as currently available on the server 110 may be a PaaS deployment and the deployment configuration of the requesting client 115 may be an IaaS deployment. Accordingly, the processor 235 determines that the medical application as currently available on the server 110 is to be transformed from PaaS deployment to IaaS deployment prior to being deployed to the database and storage facility 115-1 associated with the requesting client 115.

As another example, the requesting client may be the client 120 of FIG. 1, and the deployment configuration associated with the client 120 may be a PaaS deployment. Accordingly, because the deployment configuration of the medical application as currently available on the server 110 is a PaaS deployment, the processor 235 determines that the medical application as currently available on the server 110 need not be transformed prior to being deployed to the storage facility and data 120-1 associated with the requesting client 120.

As yet another example, the requesting client may be the client 125 of FIG. 1, and the deployment configuration associated with the client 120 may be a Local Server deployment. Accordingly, the processor 235 determines that the medical application as currently available on the server 110 is to be transformed from PaaS deployment to Local Server deployment prior to being deployed to the database and storage facility 125-1 associated with the requesting client 125.

If at S360, the processor 235 determines that the medical application as currently available on the server 110 need not be transformed, then the processor proceeds to S370, which will be further described below. However, if at S360 the processor 235 determines that the medical application as currently available on the server 110 is to be transformed, then the processor proceeds to S365.

At S365, the processor 235 transforms the medical application as currently available on the server 110 to be compatible with the deployment configuration supported by the requesting client (or each of a plurality of requesting clients, if there is more than one requesting client). The process of transforming the medical application at S365 will be described in greater detail with reference to FIG. 4.

Thereafter, at S370, the processor 235 stores at least one copy of the medical application and/or the transformed medical application in the memory 230 for possible future use/reference.

At S375, the processor 235 deploys one of the medical application or the transformed medical application (depending on the outcome of S360) to the requesting client(s). The processor 235 may deploy the medical application using any known or to be developed methods.

At S380, the processor 235 determines whether the deployment of the medical application or the transformed medical application has been successful using any known or to be developed methods. For example, various deployment checks may be performed to make sure that database(s), storage(s), back-end(s) and/or front-end(s) of the medical application have been successfully deployed. Furthermore and as part of the process performed at S380, application specific semantic checks may be performed.

The processor 235 may determine whether the deployment has been successful immediately and/or at a predetermined (and/or alternatively desired) period of time after the deployment is completed.

If at S380, the processor 235 determines that the deployment of the medical application or the transformed medical application has been successful, the process may end. However, if at S380, the processor 235 determines that the deployment of the medical application or the transformed medical application has not been successful, then at S385, the processor 235 retrieves the copy of the medical application or the copy of the transformed medical application stored at S370 and redeploys the stored copy at the database and storage facility associated with the requesting client(s).

Figure 4:
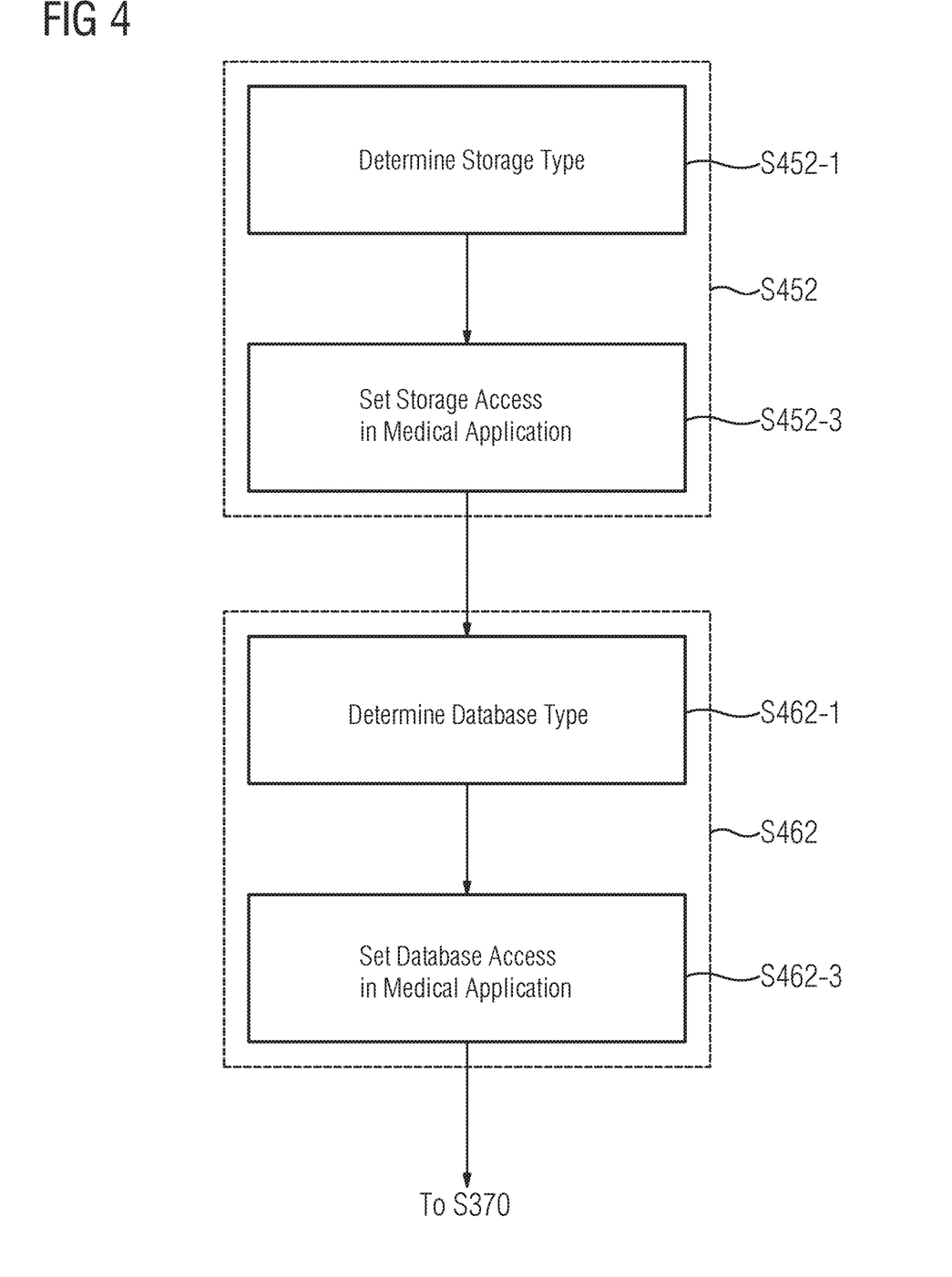
FIG. 4 is a flowchart describing a method of transforming a deployment configuration of a medical application, according to an example embodiment.

FIG. 4 is a flowchart describing a method of transforming a deployment configuration of a medical application, according to an example embodiment. The flowchart of FIG. 4 illustrates the details of the transformation discussed above with reference to S365 of FIG. 3

The transformation of a medical application (once determined to be applicable by the processor 235) includes a transformation of storage access in the medical application to correspond to the type of storage of the database and storage facility associated with the requesting client (S452) and a transformation of database access in the medical application to correspond to the type of database of the database and storage facility associated with the requesting client (S462). Each of the steps S452 and S462 will be described in more detail below.

With respect to transformation of the storage access in the medical application at S452, the processor 235, at S452-1 determines the type of storage at the database and storage facility associated with the requesting client(s). For example, if the requesting client supports IaaS deployment, then the storage may be a network attached storage. If the requesting client supports PaaS deployment, then the storage may be a PaaS blob storage. If the requesting client supports Local Access deployment, then the storage may be a local file storage. Therefore, the processor 235 determines the type of storage of the database and storage facility associated with the requesting client(s) based on the information received at S350 described above with reference to FIG. 3 (e.g., the deployment configuration supported by the requesting client(s)).

Once the processor 235 determines the type of storage at the database and storage facility associated with the requesting client(s), then at S452-3, the processor 235 sets the storage access in the medical application to access the determined storage type of the database and storage facility associated with the requesting client(s).

In one example embodiment, the processor 235 may set the storage access in the medical application via a storage abstraction layer in the medical application. In one example embodiment, the storage abstraction layer provides an application program interface (API) to upper layers for data access. As part of the API implementation data access may be performed for data stored in a local storage, data stored on a public cloud, etc. Accordingly, when a specific country's regulation require patient data storage at a local level (e.g., at a medical facility's site alone), the storage abstraction layer, via the API, may set data access for the local storage only and prevent access to, for example, a cloud storage.

With respect to transformation of the database access in the medical application at S462, the processor 235, at S462-1 determines the type of database at the database and storage facility associated with the requesting client(s). For example, if the requesting client supports IaaS deployment, then the database may be a centrally installed database. If the requesting client supports PaaS deployment, then the storage may be a PaaS managed database. If the requesting client supports Local Access deployment, then the storage may be a locally installed database. Therefore, the processor 235 determines the type of database of the database and storage facility associated with the requesting client(s) based on the information received at S350 described above with reference to FIG. 3 (e.g., the deployment configuration supported by the requesting client(s)).

Once the processor 235 determines the type of storage at the database and storage facility associated with the requesting client(s), then at S462-3, the processor 235 sets the database access in the medical application to access the determined database type of the database and storage facility associated with the requesting client(s).

In one example embodiment, the processor 235 may set the database access in the medical application via a database abstraction layer in the medical application, in a similar manner as described above.

Thereafter, the process reverts back to S370 and S370 to S385 will be performed as described above.

The method described above with reference to FIGS. 3 and 4 allow for a more flexible adjustment and/or deployment of medical applications by a vendor at various requesting clients in a more efficient and/or cost-effective manner. For example, the server 110 may have relatively more powerful and more efficient computational capabilities compared to servers used by the clients 115, 120 and/or 125. Furthermore, a memory device associated with the cloud infrastructure 105 may have a greater storage capacity compared to one or more of the database/storage devices 115-1, 120-1 and/or 125-1. Accordingly, by storing original copies of the medical applications and any associated updates at the cloud infrastructure 105, the database/storage devices associated with clients such as database/storage devices 115-1, 120-1 and 125-1 may be utilized more efficiently. Furthermore, by performing transformation of the medical application, deployment thereof, and/or updating of the medical applications by the server 110, computational burden of servers associated with and/or local to the clients 115, 120 and/or 125 may be reduced and utilized more efficiently by such clients for other purposes such as more efficient and better servicing of patients at clients, where the clients may be medical facilities as described above.

Another advantage of example embodiments described herein may be that as a result of the server being responsible for transformation, deployment, and/or updating of the medical applications, each client such as clients 115, 120 and 125 may utilize its associated network capacities (e.g., bandwidth) more efficiently.

While example embodiments have been particularly shown and described, it will be understood by one of ordinary skill in the art that variations in form and detail may be made therein without departing from the spirit and scope of the claims. The invention being thus described, it will be obvious that the same may be varied in many ways. Such variations are not to be regarded as a departure from the invention, and all such modifications are intended to be included within the scope of the invention.

I claim:

1. A remote server comprising:
a memory configured to store computer-readable instructions; and
a processor configured to execute the computer-readable instructions for installing a medical application at a target destination by
determining a deployment configuration of the target destination,
transforming the medical application into a transformed version of the medical application prior to installing the medical application at the target destination and in response to determining that the deployment configuration of the target destination is different from a deployment configuration of the medical application stored in the memory, and
deploying the transformed version of the medical application to the target destination;
wherein the transforming the medical application includes
determining a type of storage at the target destination based on the deployment configuration of the target destination,
setting storage access in the medical application to enable access to only the type of storage at the target destination, and
transforming database access in the medical application in accordance with the deployment configuration of the target destination.

2. The remote server of claim 1, wherein the deployment configuration of the target destination includes at least one of a platform as a software (PaaS) deployment, infrastructure as a software (IaaS) deployment or a local server deployment.

3. The remote server of claim 1, wherein the processor is configured to set the storage access in the medical application via a storage abstraction layer of the medical application.

4. The remote server of claim 1, wherein the type of storage at the target destination includes at least one of a platform as a service (PaaS) blob storage, network attached storage or a local file system.

5. The remote server of claim 1, wherein the processor is configured to execute the computer-readable instructions to transform the database access in the medical application by
determining a type of database at the target destination, and
setting the database access in the medical application to enable access to the type of database at the target destination.

6. The remote server of claim 5, wherein the processor is configured to set the database access in the medical application via a database abstraction layer of the medical application.

7. The remote server of claim 5, wherein the type of database at the target destination includes at least one of a platform as a service (PaaS) managed database, centrally installed database server or a locally installed database.

8. The remote server of claim 1, wherein the processor is further configured to execute the computer-readable instructions to store a copy of the transformed version of the medical application on the memory.

9. The remote server of claim 8, wherein the processor is further configured to execute the computer-readable instructions to verify successful deployment of the transformed version of the medical application.

10. The remote server of claim 9, wherein in response to a failure to verify the successful deployment of the transformed version of the medical application, the processor is configured to execute the computer-readable instructions to redeploy the copy of the transformed version of the medical application to the target destination.

11. The remote server of claim 1, wherein the processor is further configured to execute the computer-readable instructions to complete routine updates of the medical application prior to transforming the medical application, in response to determining that the medical application is to be transformed prior to deployment to the target destination.

12. The remote server of claim 1, wherein the processor is further configured to execute the computer-readable instructions to receive the deployment configuration of the target destination from an operator of the target destination.

13. The remote server of claim 1, wherein the target destination is a medical facility.

14. The remote server of claim 1, wherein the medical application is software used for maintaining, analyzing and tracking patient data.

15. The remote server of claim 1, wherein
the target destination is a hospital; and
the hospital utilizes at least one of a local server, a globally accessible server or a country-wide accessible server for obtaining and utilizing the medical application.

16. A remote server comprising:
a memory configured to store computer-readable instructions; and
a processor configured to execute the computer-readable instructions for installing a medical application at a target destination by
  determining a deployment configuration of the target destination,
  transforming the medical application into a transformed version of the medical application prior to installing the medical application at the target destination and in response to determining that the deployment configuration of the target destination is different from a deployment configuration of the medical application stored in the memory, and
  deploying the transformed version of the medical application to the target destination;
wherein the transforming the medical application includes
  determining a required type of storage at the target destination based on the deployment configuration of the target destination and storage restrictions for storing medical data associated with the target destination, and
  restricting storage access in the medical application to only the required type of storage at the target destination.

* * * * *